United States Patent
Murabayashi et al.

[11] Patent Number: 5,770,614
[45] Date of Patent: Jun. 23, 1998

[54] 2-(SUBSTITUTED PHENYL)-2-ALKOXYIMINO-N-ALKYLACETAMIDE COMPOUNDS AND FUNGICIDES CONTAINING THE SAME

[75] Inventors: Akira Murabayashi, Ibaraki; Akira Takase, Otsu; Hideyuki Takenaka, Nabari; Michio Masuko, Koka-gun, all of Japan

[73] Assignee: Shionogi & Co., Ltd., Osaka, Japan

[21] Appl. No.: 737,320

[22] PCT Filed: May 11, 1995

[86] PCT No.: PCT/JP95/00902
 § 371 Date: Nov. 12, 1996
 § 102(e) Date: Nov. 12, 1996

[87] PCT Pub. No.: WO95/32182
 PCT Pub. Date: Nov. 30, 1995

[30] Foreign Application Priority Data

May 20, 1994 [JP] Japan ................................. 6-106599
Jun. 8, 1994 [JP] Japan ................................. 6-126511
Jul. 20, 1994 [JP] Japan ................................. 6-167723

[51] Int. Cl.$^6$ ..................... A01N 43/40; C07D 213/64; C07D 213/69; C07C 251/40
[52] U.S. Cl. ..................... 514/348; 514/351; 546/291; 546/296; 546/297; 546/176; 564/164; 564/165
[58] Field of Search ..................... 564/164, 165; 546/291, 296, 297, 176; 514/312, 348, 351, 615

[56] References Cited

U.S. PATENT DOCUMENTS

5,183,921  2/1993  Takase et al. ..................... 558/301

FOREIGN PATENT DOCUMENTS

0 398 692  11/1990  European Pat. Off. .
0 596 692  5/1994  European Pat. Off. .
0 617 011  9/1994  European Pat. Off. .
3-246268  11/1991  Japan ..................... 544/286
4-182461  6/1992  Japan .
6-219986  8/1994  Japan .

OTHER PUBLICATIONS

Koehle et al., "Biokinetic properties of BAS 490 F and some related compounds", Biochem. Soc. Trans., vol. 22, No. 1, pp. 65S, 1993.

Urashima et al., "Varietal resistance and chemical control of wheat blast fungus", Summa Phytopathol., vol. 20, No. 2, pp. 107–112, 1994.

*Primary Examiner*—Alan L. Rotman
*Attorney, Agent, or Firm*—Foley & Lardner

[57] ABSTRACT

A novel 2-(substituted phenyl)-2-alkoxyiino-N-alkylacetamide compounds having a wide fungicidal spectrum and especially an excellent activity of controlling *Pseudocercosporella herpotrichoides*; and a composition containing the compound for controlling *Pseudocercosporella herpotrichoides*.

8 Claims, No Drawings

2-(SUBSTITUTED PHENYL)-2-ALKOXYIMINO-N-ALKYLACETAMIDE COMPOUNDS AND FUNGICIDES CONTAINING THE SAME

CROSS-REFERENCE

This application is a 371 of PCT/JP95/00902 filed May 11, 1995.

TECHNICAL FIELD

The present invention relates to 2-(substituted phenyl)-2-alkoxyimino-N-alkylacetamide compounds and fungicides containing them, in particular, a composition for controlling *Pseudocercosporella herpotrichoides*.

BACKGROUND OF THE INVENTION

Certain alkoxyiminoacetamide derivatives are known to have fungicidal activity against certain pathogens (JP-A 3-246268, JP-A 4-182461). However, their fungicidal activity against wheat eyespot (*Pseudocercosporella herpotrichoides*), which is a serious pathogen of wheat, has not been known.

The present invention is to provide a novel compound which has a broad fungicidal spectrum and potent controlling activity particularly against *Pseudocercosporella herpotrichoides*, and a novel composition to control *Pseudocercosporella herpotrichoides*.

DISCLOSURE OF THE INVENTION

The present inventors have intensively studied to achieve the above object. As a result, it has been found that 2-(substituted phenyl)-2-alkoxyimino-N-alkylacetamide compounds have potent fungicidal activity against *Pseudocercosporella herpotrichoides* and that a novel 2-(substituted phenyl)-2-methoxyimino-N-methylacetamide compound included in the above compounds has not only potent fungicidal activity against *Pseudocercosporella herpotrichoides* but also a broad fungicidal spectrum. Thus, the present invention has been completed.

The present invention provides:

(1) A compound of the formula (I-A):

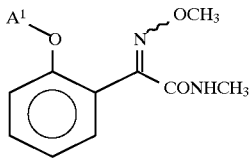

wherein $A^1$ is 3,4-dimethylphenyl or 3,5-dimethylphenyl, and ~ indicates a configuration of an E- or Z-isomer or a mixture thereof;

(2) A compound of the formula (I-B):

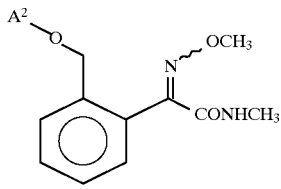

wherein $A^2$ is 3-chloro-2-pyridyl, 5-chloro-2-pyridyl, 3-trifluoromethyl-2-pyridyl, 4-trifluoromethyl-2-pyridyl, 6-trifluoromethyl-2-pyridyl, 6-methoxy-2-pyridyl, 6-isopropoxy-2-pyridyl, 6-methylthio-2-pyridyl, 5-chloro-3-trifluoromethyl-2-pyridyl, 6-methoxy-3-trifluoromethyl-2-pyridyl, 6-isopropoxy-3-trifluoromethyl-2-pyridyl,6-chloro-4-trifluoromethyl-2-pyridyl, 3,5,6-trichloro-4-trifluoromethyl-2-pyridyl, 6-chloro-3,5-di(trifluoromethyl)-2-pyridyl, 6-methoxy-5-trifluoromethyl-2-pyridyl, 6-isopropoxy-5-trifluoromethyl-2-pyridyl, 6-methylamino-5-trifluoromethyl-2-pyridyl, 3,6-dichloro-5-trifluoromethyl-2-pyridyl or 2-quinolyl, and ~ indicates a configuration of an E- or Z-isomer or a mixture thereof, or a salt thereof;

(3) A compound according to the above item (2), wherein $A^2$ is 3-trifluoromethyl-2-pyridyl or 5-chloro-3-trifluoromethyl-2-pyridyl, or a salt thereof;

(4) A fungicidal composition which comprises as an active ingredient a compound of the formula (I-A) or (I-B) or a salt thereof;

(5) A composition for controlling *Pseudocercosporella herpotrichoides*, which comprises as an active ingredient a compound of the formula (I-A) or (I-B) or a salt thereof;

(6) A composition for controlling *Pseudocercosporella herpotrichoides*, which comprises as an active ingredient a compound of the formula (I):

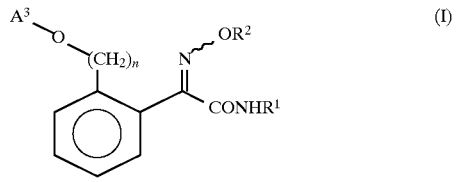

wherein $A^3$ is optionally substituted phenyl, optionally substituted pyridyl or optionally substituted quinolyl, $R^1$ and $R^2$ are the same or different and are alkyl, n is 0 or 1, and ~ indicates a configuration of an E- or Z-isomer or a mixture thereof, or a salt thereof; and (7) A composition according to the above item (6), wherein $R^1$ and $R^2$ are methyl.

The term "lower" used herein means having 1 to 8 carbon atoms, preferably 1 to 6 carbon atoms, more preferably 1 to 4 carbon atoms, unless otherwise indicated.

$A^2$ in the formula (I-B) is preferably 3-trifluoromethyl-2-pyridyl or 5-chloro-3-trifluoromethyl-2-pyridyl.

The optionally substituted pyridyl and optionally substituted quinolyl represented by $A^3$ in the formula (I) may have a bond to the oxygen atom at any possible position, but preferably they have the bond at the 2-position.

Each of the optionally substituted phenyl, optionally substituted pyridyl and optionally substituted quinolyl represented by $A^3$ is unsubstituted or substituted by 1 to 5 substituents, preferably 1 to 4 substituents, more preferably 1 to 3 substituents, at any possible position.

The substituent is selected from, for example, lower alkyl (e.g., methyl, ethyl, propyl, butyl, etc.), lower alkenyl (e.g., vinyl, allyl, crotyl, etc.), lower alkynyl (e.g., ethynyl, propargyl, butynyl, etc.), cycloalkyl (e.g., cyclopropyl, cyclopentyl, cyclohexyl, etc.), cycloalkenyl (e.g., cyclopentenyl, cyclohexenyl, etc.), lower alkanoyl (e.g., acetyl, propionyl, isobutyryl, etc.), lower alkylsilyl (e.g., methylsilyl, ethylsilyl, propylsilyl, butylsilyl, etc.), halogenated lower alkyl (e.g., trifluoromethyl, trichloromethyl, chloromethyl, 2-bromoethyl, 1,2-dichloropropyl, etc.), (lower)alkylamino (e.g., methylamino, ethylamino, etc.), di(lower)alkylamino (e.g., dimethylamino, diethylamino, etc.), (lower)alkylthio (e.g., methylthio, ethylthio, etc.), phenyl, phenyl(lower)alkyl (e.g., benzyl, phenethyl, etc.), phenyl(lower)alkenyl (e.g., styryl, cinnamyl, etc.), furyl (lower)alkyl (e.g., 3-furylmethyl, 2-furylethyl, etc.), furyl (lower)alkenyl (e.g., 3-furylvinyl, 2-furylallyl, etc.), halogen (e.g., fluorine, chlorine, bromine, iodine), nitro, cyano, —OR$^4$ [wherein R$^4$ is hydrogen, lower alkyl (e.g., methyl, ethyl, propyl, etc.), lower alkenyl (e.g., vinyl, allyl, crotyl, etc.), lower alkynyl (e.g., ethynyl, 2-propynyl, 3-butynyl, etc.), lower alkanoyl (e.g., acetyl, propionyl, butyryl, etc.), phenyl, lower alkoxyphenyl (e.g., 3-methoxyphenyl, 4-ethoxyphenyl, etc.), nitrophenyl (e.g., 3-nitrophenyl, 4-nitrophenyl, etc.), phenyl(lower)alkyl (e.g., benzyl, phenethyl, phenylpropyl, etc.), cyanophenyl(lower)alkyl (e.g., 3-cyanophenylmethyl, 4-cyanophenylethyl, etc.), benzoyl, tetrahydropyranyl, pyridyl, trifluoromethylpyridyl, pyrimidinyl, benzothiazolyl, quinolyl, benzoyl(lower)alkyl (e.g., benzoylmethyl, benzoylethyl, etc.), benzensulfonyl, or lower alkylbenzenesulfonyl (e.g., toluenesulfonyl, etc.)], —CH$_2$—Z—R$^5$ [wherein Z is —O—, —S— or —NR$^6$— (in which R$^6$ is hydrogen or lower alkyl), R$^5$ is phenyl, halophenyl (e.g., 2-chlorophenyl, 4-fluorophenyl, etc.), lower alkoxyphenyl (e.g., 2-methoxyphenyl, 4-ethoxyphenyl, etc.), pyridyl, or pyrimidinyl], etc. In particular, halogen, lower alkyl, halogenated lower alkyl, lower alkoxy, lower alkylthio and lower alkylamino are preferred.

Examples of the alkyl represented by R$^1$ and R$^2$ include alkyl having 1 to 6 carbon atoms, preferably 1 to 4 carbon atoms, such as methyl, ethyl, propyl, isopropyl, butyl, isobutyl, t-butyl, etc. In particular, methyl and ethyl are preferred, and methyl is particularly preferred.

The compound of the formula (I-A), (I-B) or (I) is any of its E- or Z-isomer and a mixture thereof. This is indicated by the wave line ~ in the formulas. Each of these compounds is preferably its E-isomer because the E-isomer has more potent fungicidal activity.

The compound of the formula (I) is preferably the compound of the formula (I-A) or (I-B).

Below are the preferred processes for producing the compound of the formula (I) including a compound of the formula (I-A) or (I-B).

The compound of the formula (I) wherein n is 0 (i.e. the compound (V) in Scheme 1) can be prepared, for example, according to Scheme 1.

Scheme 1

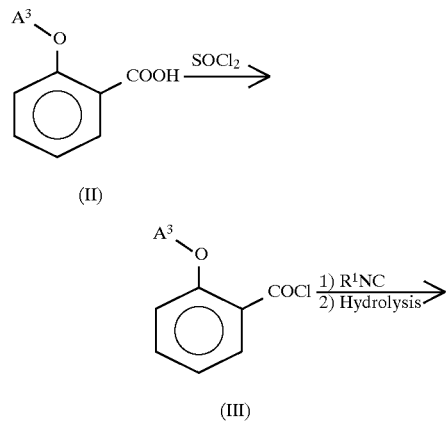

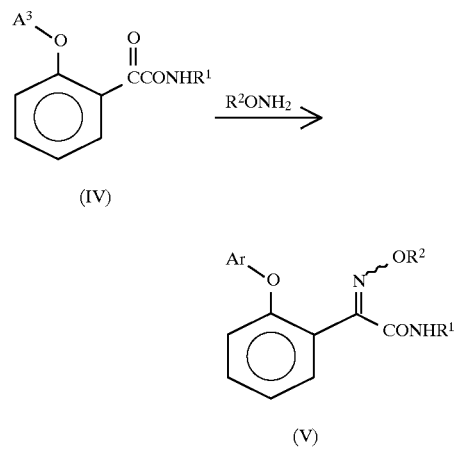

wherein each symbol is as defined above, and A$^3$ is preferably A$^1$, and R$^1$ and R$^2$ are preferably methyl.

That is, the carboxylic acid (II) is reacted with thionyl chloride or phosgene in a solvent such as a hydrocarbon (e.g., benzene, toluene, etc.) to give the acid chloride (III). Then, the resulting acid chloride (III) is subjected to condensation reaction with an alkyl isocyanide (e.g. methyl isocyanide, etc.) in the absence of a solvent or in an inert solvent (e.g., benzene, toluene, etc.). The resulting compound is then subjected to hydrolysis in the presence or absence of a base (e.g., sodium hydroxide, etc.) or an acid (e.g., hydrochloric acid, etc.), if necessary in a hydrophilic solvent (e.g., acetone, tetrahydrofuran, etc.), to give the α-ketoamide (IV) (see JP-A 5-331124). The resulting α-ketoamide (IV) is then reacted with an alkoxyamine (e.g., methoxylamine, etc.) or a salt thereof in an alcoholic solvent (e.g., methanol, etc.) to give the desired compound (V) (see JP-A 3-246268). The compound (V) thus obtained can be separated and purified by conventional methods (e.g., chromatography, recrystallization, etc.).

The compound of the formula (I) wherein n is 1 can be prepared, for example, by the method shown in Scheme 2 below. Scheme 2 illustrates the preparation of the compound (VIII) having optionally substituted 6-substituted-2-pyridyl as A$^3$ in the formula (I), but the compound (VIII) having other optionally substituted pyridyl, optionally substituted phenyl or optionally substituted quinolyl as A$^3$ can be prepared in a similar manner.

Scheme 2

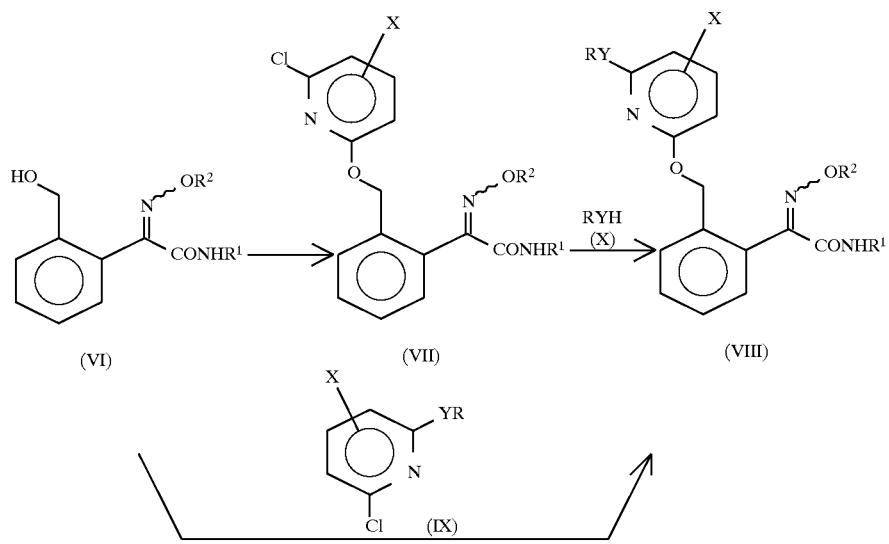

wherein X is hydrogen or a substituent of $A^3$ described above, R is alkyl (e.g., methyl, ethyl, n-propyl, isopropyl, butyl, etc.), Y is an oxygen atom, a sulfur atom or R'N (in which R' is hydrogen or alkyl such as methyl, ethyl, propyl, butyl, etc.), and the other symbols are as defined above.

First, the compound (VI) is reacted with optionally substituted 2,6-dichloropyridine in a solvent (e.g., dimethylformamide, tetrahydrofuran, etc.) in the presence of a base [e.g., sodium hydride, alkali carbonate (e.g., sodium carbonate, potassium carbonate, etc.), alkali hydroxide (e.g., sodium hydroxide, potassium hydroxide, etc), etc.] to give the compound (VII) (see JP-A 3-246268, JP-A 4-182461). Then, the resulting compound (VII) is reacted with the compound (X) or a metal salt thereof in an organic solvent or water-containing organic solvent (e.g., methanol, ethanol, tetrahydrofuran, etc.) to give the desired compound (VIII). The amount of the compound (X) to be used is 1 to 3 mol, preferably 1.0 to 1.2 mol, per mol of the compound (VII). The reaction temperature is 0° to 120° C., preferably 50° to 100° C., and the reaction time is 1 hour to 30 hours, preferably 5 hours to 20 hours.

Alternatively, the compound (VIII) can be prepared by reacting the compound (VI) with the compound (IX) according to the method described in JP-A 3-24628 or JP-A 4-182461.

The compound (VIII) thus obtained can be separated and purified by conventional methods (e.g., chromatography, recrystallization, etc.).

The compound of the formula (I) used in the present invention has potent fungicidal activity against *Pseudocercosporella herpotrichoides* and is useful as a composition for controlling *Pseudocercosporella herpotrichoides*.

The compound of the formula (I-A) or (I-B) of the present invention exhibits potent fungicidal activity against *Pseudocercosporella herpotrichoides*. It is also effective against a wide range of phytopathogenic fungi on crop plants (e.g., rice, wheat, barley, rye, corn, common millet, millet, buckwheat, soybean, redbean, peanut, etc.), fruit trees (e.g., citrus fruits, grape, apple, pear, peach, etc.), vegetables (e.g., cucumber, eggplant, tomato, pumpkin, kidney bean, etc.), etc., or seeds thereof. It is also effective against phytopathogenic fungi in soil. Thus, it has a broad fungicidal spectrum. Specifically, it shows potent fungicidal activity against *Pseudocercosporella herpotrichoides, Pyricularia oryzae, Rhizoctonia solani, Erysiphe graminis, Puccinia spp., Sphaerotheca fulipinea, Erysiphe cichoracearum, Phytophthora infestans, Pseudoperonospora cubensis, Peronospora manshurica, Plasmopara viticola, Botrytis cinerea* of vegetables, grape, etc., *Pythium aphanidermatum, Sclerotinia sclerotiorum* of buckwheat, soybean, colza, etc., *Corticium rolfsii* of soybean, redbean, potato, peanut, etc. Therefore, the compound of the formula (I-A) or (I-B) is useful as fungicides, particularly as agricultural fungicides, preferably as a composition for controlling *Pseudocercosporella herpotrichoides*.

Application of the compound of the formula (I) used in the present invention (including the compound of the formula (I-A) or (I-B)) may be made to plants by any conventional procedure such as spraying, scattering or spreading of the active compound. Application may also be made through treatment of seeds of plants, soil where plants grow, soil where seeds are sown, paddy field or water for perfusion with the active compound. Application may be performed before or after the infection with phytopathogenic fungi on plants.

The compound can be used in a conventional formulation form suitable for agricultural fungicides such as solutions, wettable powders, emulsions, suspensions, concentrated liquid preparations, tablets, granules, aerosols, powders, pastes, dusts, etc.

Such formulation form can be prepared in a conventional manner by mixing at least one compound of the present invention with an appropriate solid or liquid carrier(s) and, if necessary, an appropriate adjuvant(s) (e.g., surfactants, spreaders, dispersants, stabilizers, etc.) for improving the dispersibility and other properties of the active ingredient.

Examples of the solid carriers or diluents include botanical materials (e.g., flour, tobacco stalk powder, soybean powder, walnut-shell powder, vegetable powder, saw dust, bran, bark powder, cellulose powder, vegetable extract residue), fibrous materials (e.g., paper, corrugated cardboard, old rags), artificial plastic powders, clays (e.g., kaolin, bentonite, fuller's earth), talc, other inorganic materials (pyrophyllite, sericite, pumice, sulfur powder, active carbon), chemical fertilizers (e.g., ammonium sulfate, ammonium phosphate, ammonium nitrate, urea, ammonium chloride), etc.

Examples of the liquid carriers or diluents include water, alcohols (e.g., methanol, ethanol), ketones (e.g., acetone, methyl ethyl ketone), ethers (e.g., diethyl ether, dioxane, cellosolve, tetrahydrofuran), aromatic hydrocarbons (e.g., benzene, toluene, xylene, methylnaphthalene), aliphatic hydrocarbons (e.g., gasoline, kerosene, lamp oil), esters, nitrites, acid amides (e.g., dimethylformamide, dimethylacetamide, etc.), halogenated hydrocarbons (e.g., dichloroethane, carbon tetrachloride), etc.

Examples of the surfactants include alkyl sulfates, alkyl sulfonates, alkylaryl sulfonates, polyethylene glycol ethers, polyhydric alcohol esters, etc.

Examples of the spreaders or dispersants include casein, gelatin, starch powder, carboxymethyl cellulose, gum arabic, alginic acid, lignin, bentonite, molasses, polyvinyl alcohol, pine oil, agar, etc.

Examples of the stabilizers include PAP (a mixture of isopropylphosphate), tricresyl phosphate (TCP), tolu oil, epoxidized oil, surfactants, fatty acids and their esters, etc.

The composition of the present invention may contain other fungicides, insecticides, herbicides or fertilizers in addition to the above ingredients.

In general, the above composition contains at least one compound of the formula (I) of the present invention in a concentration of 1 to 95% by weight, preferably 2.0 to 80% by weight. The composition can be used as such or in a diluted form. About 1.0 g to 5 kg/hectare, preferably about 2 g to 100 g/hectare, of the compound of the present invention is used in a concentration of normally about 1 to 50,000 ppm, preferably about 100 to 5,000 ppm.

EXAMPLES

The following experiments and test examples further illustrate the present invention in detail, but are not to be construed to limit the scope thereof.

Example 1

Synthesis of (E)-2-[2-(6-methoxypyridin-2-yloxymethyl)phenyl]-2-methoxyimino-N-methylacetamide (Compound No. 6)

28% sodium methoxide—methanol solution (1.16 g) was added to (E)-2-[2-(6-chloropyridin-2-yloxymethyl)phenyl]-2-methoxyimino-N-methylacetamide (400 mg), and the mixture was heated under reflux with stirring for 4 hours. The mixture was neutralized with 1N hydrochloric acid, and water was added. The mixture was extracted with ethyl acetate. The organic layer was washed with saturated brine and dried, and the solvent was evaporated. The resulting oil was purified by column chromatography on silica gel to give the title compound (61 mg). mp. 81°–82° C.

Example 2

Synthesis of (E)-2-[2-(6-methylthiopyridin-2-yloxymethyl)phenyl]-2-methoxyimino-N-methylacetamide (Compound 8)

(E)-2-[2-(6-chloropyridin-2-yloxymethyl)phenyl]-2-methoxyimino-N-methylacetamide (1.2 g) was dissolved in tetrahydrofuran (10 ml), and sodium thiomethoxide (1 g) was added. The mixture was heated under reflux with stirring for 5 hours. Water was added, and the mixture was extracted with ethyl acetate. The organic layer was washed with saturated brine and dried, and the solvent was evaporated. The resulting oil was purified by column chromatography on silica gel to give the title compound (800 mg). mp. 130°–132° C.

Example 3

Synthesis of (E)-2-[2-(6-methylamino-5-trifluoromethylpyridin-2-yloxymethyl)phenyl]-2-methoxyimino-N-methylacetamide (Compound No. 17)

A 40% methylamine—methanol solution (10 ml) was added to (E)-2-[2-(6-chloro-5-trifluoromethylpyridin-2-yloxymethyl)phenyl]-2-methoxyimino-N-methylacetamide (402 mg), and the mixture was stirred at 100° C. for 17 hours. Water was added, and the mixture was extracted with ethyl acetate. The organic layer was washed with saturated brine and dried, and then the solvent was evaporated. The resulting oil was purified by column chromatography on silica gel to give the title compound (379 mg). mp. 66°–67° C.

Example 4

In the same manner as that described above, the compounds in Table 1 were synthesized. All the compounds in Table 1 are E-isomers. In Table 1, the physical properties of the compounds obtained in Examples above are also listed.

TABLE 1

| Compound No. | $R^3$ | NMR | mp (°C.) |
|---|---|---|---|
| 1 | 3-Cl | | δ2.90 (3H, d (J=5.8 Hz)) |
| | | | δ3.94 (3H, s) |
| 2 | 5-Cl | | 117.5~118.5 |
| 3 | 3-CF$_3$ | | 96~97 |
| 4 | 4-CF$_3$ | | 108~109 |
| 5 | 6-CF$_3$ | | 68~69 |
| 6 | 6-OCH$_3$ | | 81~82 |
| 7 | 6-O$^i$C$_3$H$_7$ | | 115~120 |
| 8 | 6-SCH$_3$ | | 130~132 |
| 9 | 3-CF$_3$, 5-Cl | | 105~106 |
| 10 | 3-CF$_3$, 6-OCH$_3$ | | 126~130 |
| 11 | 3-CF$_3$, 6-O$^i$C$_3$H$_7$ | | 126~129 |
| 12 | 4-CF$_3$, 6-Cl | | 114.5~117.5 |
| 13 | 4-CF$_3$, 3,5,6-Cl$_3$ | | 119~120 |
| 14 | 3,5-(CF$_3$)$_2$, 6-Cl | | 115.5~156 |
| 15 | 5-CF$_3$, OCH$_3$ | | 123~125 |
| 16 | 5-CF$_3$, O$^i$C$_3$H$_7$ | | 124~127 |
| 17 | 5-CF$_3$, 6-NHCH$_3$ | | 66~67 |
| 18 | 5-CF$_3$, 3,6-Cl$_2$ | | 141~141.5 |

Example 5

Synthesis of (E)-2-[2-(3,4-dimethylphenoxy)-phenyl]-2-methoxyimino-N-methylacetamide (E)-2-(3,4-dimethylphenoxy)benzoic acid (3.0 g) was suspended in toluene (7 ml), and thionyl chloride (1.62 g) and 3 drops of dimethylformamide were added. The mixture was stirred at 60° C. for 1 hour. Toluene was evaporated under reduced pressure, methyl isocyanide (610 mg) was added, and the mixture was stirred at 60° C. overnight. Methyl isocyanide (610 mg) was further added, and the mixture was stirred for 2 hours. 5N hydrochloric acid (10 ml) and acetone (13 ml) were added, and the mixture was stirred for 2 hours. Water was added, and the mixture was extracted with ethyl acetate. The organic layer was washed with saturated brine and dried, and then the solvent was evaporated. The resulting oil was purified by column chromatography on silica gel to give (E)-2-[2-(3,4-dimethylphenoxy)phenyl]-2-oxo-N-methylacetamide(2.98 g).

$^1$H-NMR (CDCl$_3$) ppm: 2.23(6H,s), 2.88(3H,d,J=4.9Hz), 6.60(1H,brs), 6.74(3H,m), 7.09(1H,d,J=7.9Hz), 7.12(1H,td, J=7.9,1.2Hz), 7.42(1H,td,J=7.3,1.8Hz)(1H,dd,J=7.3,1.8Hz).

(E)-2-[2-(3,4-dimethylphenoxy)phenyl]-2-oxo-N-methylacetamide (2.58 g) and methoxylamine hydrochloride (916 mg) were dissolved in methanol (50 ml), and the mixture was heated under reflux with stirring overnight. Water was added, and the mixture was extracted with ethyl acetate. The organic layer was washed with saturated brine and dried, and then the solvent was evaporated. The resulting oil was purified by column chromatography on silica gel to give the title compound (2.00 g). mp. 98°–100° C.

Example 6

Synthesis of (E)-2-[2-(3,5-dimethylphenoxy)-phenyl]-2-methoxyimino-N-methylacetamide 2-(3,5-Dimethylphenoxy)benzoic acid (3.00 g) was suspended in toluene (7 ml), and thionyl chloride (1.62 g) and 3 drops of dimethylformamide were added. The mixture was stirred at 60° C. for 1 hour. Toluene was evaporated under reduced pressure, methyl isocyanide (1.00 g) was added, and the mixture was stirred at 60° C. overnight. 5N hydrochloric acid (10 ml) and acetone (13 ml) were added, and the mixture was stirred for 2 hours. Water was added, and the mixture was extracted with ethyl acetate. The organic layer was washed with saturated brine and dried, and then the solvent was evaporated. The resulting oil was purified by column chromatography on silica gel to give 2-[2-(3,5-dimethylphenoxy)phenyl]-2-oxo-N-methylacetamide (2.28 g).

$^1$H-NMR (CDCl$_3$) ppm: 2.28(3H,s), 2.88(3H,d,J=4.8Hz), 6.61(1H,brs), 6.68(2H,s), 6.78(1H,s), 6.87(1H,d,J=7.3Hz), 7.14(1H,td,J=7.3,1.2Hz), 7.44(1H,td,J=7.3,1.8Hz), 7.74(1H, dd,J=7.3,1.8Hz).

2-[2-(3,5-dimethylphenoxy)phenyl]-2-oxo-N-methyl-acetamide (2.58 g) and methoxylamine hydrochloride (1.52 g) were dissolved in methanol (50 ml), and the mixture was heated under reflux with stirring overnight. Water was added, and the mixture was extracted with ethyl acetate. The organic layer was washed with saturated brine and dried, and then the solvent was evaporated. The resulting oil was purified by column chromatography on silica gel to give the title compound (1.96 g). mp. 90°–91° C.

Example 7

Synthesis of (E)-2-[2-(2-quinolinyloxymethyl) phenyl]-2-methoxyimino-N-methylacetamide (E)-2-[2-(hydroxymethyl)phenyl]-2-methoxyimino-N-methylacetamide (0.44 g, 2 mmol) was dissolved in dry DMF (4 ml). 60% sodium hydride (0.10 g, 2.4 mmol) was added at room temperature, the mixture was stirred for 10 minutes, and then 2-chloroquinoline (0.36 g, 2.2 mmol) was added at room temperature. The resulting mixture was allowed to stand at room temperature overnight, and saturated brine was added. The mixture was extracted with ethyl acetate and dried over magnesium sulfate, and the solvent was evaporated under reduced pressure. The resulting crude product was purified by column chromatography on silica gel (ethyl acetate—n-hexane) to give the title compound (0.46 g) as an oil.

$^1$H-NMR (in CDCl$_3$) ppm: 2.88(1H,d,J=4.9Hz), 3.93 (3H, s), 5.43(2H,s), 6.64(1H,br s), 6.86(1H,d,J=8.8Hz), 7.25(1H, m), 7.34–7.45(3H,m), 7.59–7.69(2H,m), 7.71 (1H,d,J=7.8Hz), 7.83(1H,d,J=7.8Hz), 8.00(1H,d,J=8.8Hz).

The following pot experiments illustrate the controlling effects of foliage application of the various compounds of the present invention on various plant diseases.

Experimental Method

All the tests were made for evaluation of controlling (preventive) effects except the test for *Pseudocercosporella herpotrichoides*. That is, the tests were carried out by spraying a liquid sample to a test plant and inoculating the plant with a pathogen 24 hours thereafter. A test compound was dissolved in a small amount of N,N-dimethylformamide, and the solution was diluted to a given concentration with distilled water containing a spreader to prepare a liquid sample. The percent control was calculated according to the following equation:

Percent control (%)={(severity, number of lesions, etc. in untreated plot—severity, number of lesions, etc. in treated plot)/severity, number of lesions, etc. in untreated plot}×100

Test Example 1

Controlling Effect on *Pseudocercosporella herpotrichoides*

The seeds of wheat (cv.: NORIN No. 61) were sown in plastic pots (each 11 cm in diameter), followed by cultivation at 15° C. for 1 week. *Pseudocercosporella herpotrichoides* cultured on sterilized oat seeds was put together with the seeds at the base of the wheat stem to inoculate the test plant with the pathogen. After the inoculation, the test plant was grown for further 3 weeks in the same greenhouse. When homogeneous development of the disease was observed at the lower part of the stem of the wheat seedlings, a solution or suspension of the test compound was sprayed. After the treatment, the test plant was grown for further 4 weeks in the same greenhouse, and then the severity of the disease was checked. Compound A is (E)-2-[2-(5-trifluoromethylpyridin-2-yloxymethyl)phenyl]-2-methoxyimino-N-methylacetamide (see JP-A 3-246268). Compound B is (E)-2-[2-(6-chloropyridin-2-yloxymethyl)phenyl]-2-methoxyimino-N-methylacetamide (see JP-A 4-182461). The wheat seedlings were pulled up to assess the lesion expansion of the first internode of the stem. The criteria for the assessment was grouped into 5 grades, and the severity of the disease was determined to calculate the percent control. The results are shown in Table 2.

TABLE 2

| | Controlling effect on *Pseudocercosporella herpotrichoides* by foliage application (percent control (%)) | | |
|---|---|---|---|
| Compound No. | 250 ppm | 125 ppm | 62.5 ppm |
| 3 | 82 | 63 | 46 |
| 9 | 82 | 68 | 51 |
| Compound A | 45 | 24 | 13 |
| Compound B | 28 | 21 | 24 |

Test Example 2

Controlling effect on *Pyricularia oryzae*

Two-week rice seedlings (cv.: AICHIASAHI) were transplanted in plastic cups (each 9 cm in diameter) and cultivated further 2 weeks. A solution or suspension of the test compound was sprayed to the foliage of the rice seedlings. The inoculation of the pathogen was carried out by spraying to the treated foliage a conidia suspension of *Pyricularia oryzae* cultured in an oatmeal medium. After the inoculation, the test plant was kept in a moist chamber (28° C., 100% R.H.) for 24 hours and then in a greenhouse for 5 days. Six days after the inoculation, the number of lesions on the leaves of the inoculated plant was measured to calculate the percent control. The results are shown in Table 3.

TABLE 3

| Compound No. | Controlling effect on *Pyricularia oryzae* by foliage application at 500 ppm (percent control (%)) |
| --- | --- |
| 1 | 97 |
| 2 | 97 |
| 3 | 100 |
| 4 | 90 |
| 5 | 100 |
| 6 | 90 |
| 7 | 97 |
| 9 | 100 |
| 10 | 97 |
| 11 | 97 |
| 12 | 90 |
| 14 | 97 |
| 15 | 97 |
| 16 | 90 |
| 18 | 97 |

Test Example 3

Controlling Effect on Cucumber Powdery Mildew (*Sphaerotheca fuliginea*)

Seeds of cucumber (cv.: TSUKUBASHIROIBO) were sown in plastic cups (each 9 cm in diameter), followed by cultivation for 2 to 3 weeks. A solution or suspension of the test compound was sprayed on the surface of their first leaves. The pathogen was inoculated by spraying to the treated leaves a conidia suspension of *Sphaerotheca fuliginea* which had been cultured on the cucumber leaves. After the inoculation, the plants were kept in a greenhouse at 20° C. Ten days after the inoculation, the infected area on the leaf was observed, and the percent control was calculated. The results are shown in Table 4.

TABLE 4

| Compound No. | Controlling effect on *Sphaerotheca fuliginea* by foliage application at 500 ppm (percent control (%)) |
| --- | --- |
| 1 | 100 |
| 2 | 100 |
| 3 | 100 |
| 4 | 100 |
| 5 | 100 |
| 6 | 100 |
| 7 | 100 |
| 8 | 100 |
| 9 | 100 |
| 10 | 100 |
| 11 | 100 |
| 12 | 100 |
| 13 | 100 |
| 14 | 100 |
| 15 | 100 |
| 16 | 100 |
| 18 | 100 |

Test Example 4

Controlling Effect on *Botrytis cinerea*

The seeds of cucumber (cv.: TSUKUBASHIROIBO) were sown in plastic cups (each 9 cm in diameter), followed by cultivation for 2 to 3 weeks. A solution or suspension of the test compound was sprayed to the surface of their first leaves, and mycelial disks of *Botrytis cinerea* cultured on the potato sucrose agar medium were put on the treated leaf surface to inoculate the seedlings with the pathogen. After the inoculation, the plants were kept in a moist chamber at 20° C. for 2 days. The diameter of the lesions around the inoculum was measured and the percent control was calculated. The results are shown in Table 5.

TABLE 5

| Compound No. | Controlling effect on *Botrytis cinerea* by foliage application at 500 ppm (percent control (%)) |
| --- | --- |
| 1 | 70 |
| 2 | 70 |
| 3 | 70 |
| 5 | 70 |
| 9 | 70 |

Test Example 5

Controlling Effect on *Pseudoperonospora cubensis*

The seeds of cucumber (cv.: TSUKUBASHIROIBO) were sown in plastic cups (each 9 cm in diameter), followed by cultivation for 2 to 3 weeks. A solution or suspension of the test compound was sprayed to the surface of their first leaves, and a zoosporangia suspension of *Pseudoperonospora cubensis* cultured on cucumber leaves was dropped on the treated leaf surfaces to inoculate the test plants with the pathogen. After the inoculation, the plants were kept in a moist chamber at 20° C. for 10 days. Then, the increased diameters of the lesions around the inoculated part were measured and the percent control was calculated. The results are shown in Table 6.

TABLE 6

| Compound No. | Controlling effect on *Pseudoperonospora cubensis* by foliage application at 500 ppm (percent control (%)) |
| --- | --- |
| 1 | 100 |
| 2 | 100 |
| 3 | 100 |
| 4 | 100 |
| 5 | 100 |
| 6 | 100 |
| 8 | 100 |
| 9 | 100 |
| 10 | 100 |
| 11 | 100 |
| 12 | 100 |
| 13 | 90 |
| 14 | 100 |
| 15 | 90 |
| 16 | 100 |
| 18 | 100 |

Test Example 6

Controlling Effect on *Erysiphe graminis* f. sp. tritici

The seeds of wheat (cv.: NORIN No. 61) were sown in plastic cups (each 9 cm in diameter), followed by cultivation for 2 to 3 weeks. A solution or suspension of the test compound was sprayed to the seedlings, and conidia of *Erysiphe graminis* f. sp. tritici cultured on wheat leaves were dropped on the treated test plants to inoculate the plants with the pathogen. After the inoculation, the plants were kept in a greenhouse at 20° C. Ten days after the inoculation, the infected area on the inoculated leaf was observed, and the percent control was calculated. The results are shown in Table 7.

TABLE 7

| Compound No. | Controlling effect on *Erysiphe graminis* f. sp. *tritici* by foliage application at 500 ppm (percent control (%)) |
|---|---|
| 1 | 100 |
| 2 | 99 |
| 3 | 97 |
| 4 | 90 |
| 5 | 100 |
| 6 | 100 |
| 7 | 97 |
| 8 | 97 |
| 9 | 100 |
| 10 | 97 |
| 11 | 97 |
| 12 | 90 |
| 13 | 90 |
| 14 | 100 |
| 15 | 97 |
| 16 | 97 |
| 18 | 90 |

Test Example 7

Controlling Effect on *Puccinia coronata*

The seeds of oat (cv.: PC-38) were sown in plastic cups (each 9 cm in diameter), followed by cultivation for 2 weeks. A solution or suspension of the test compound was sprayed to the seedlings. Spores of *Puccinia coronata* cultured on oat leaves were diluted about 5-fold (by weight) with talc, and sprayed to the treated test plants to inoculate the plants with the pathogen. After the inoculation, the plants were kept in a moist chamber at 20° C. for 1 day and then in a greenhouse for 9 days. The infected area on the leaf was observed, and the percent control was calculated. The results are shown in Table 8.

TABLE 8

| Compound No. | Controlling effect on *Puccinia coronata* by foliage application at 500 ppm (percent control (%)) |
|---|---|
| 1 | 100 |
| 2 | 99 |
| 5 | 100 |
| 6 | 97 |
| 7 | 100 |
| 8 | 90 |
| 9 | 100 |
| 10 | 97 |
| 11 | 97 |
| 15 | 100 |
| 16 | 97 |
| 18 | 90 |

It is clear from Table 2 that the compound of the present invention shows very potent controlling activity against *Pseudocercosporella herpotrichoides*, which has been very-difficult to control. In addition, Tables 3 to 8 clearly show that the compound of the present invention has a very broad fungicidal spectrum and exhibits potent controlling activity against many diseases caused by oomycetes, basidiomycetes, ascomycetes, deuteromycetes, etc.

Thus, by applying the compound of the present invention to e.g. *Pseudocercosporella herpotrichoides*, which has been very difficult to control, the compound of the present invention can control not only *Pseudocercosporella herpotrichoides* but also powdery mildew and rust, which are important diseases of wheat, barley, oats, rye, etc. and have become problematic because of the appearance of their resistant cells. The compound of the invention can thus become a very useful drug to control diseases in cultivation of wheat, barley, oats, rye, etc.

The present invention thus provides novel compounds having a broad fungicidal spectrum and potent fungicidal activity particularly against *Pseudocercosporella herpotrichoides*, and a novel composition for controlling *Pseudocercosporella herpotrichoides*.

We claim:

1. A compound of the formula (I-B):

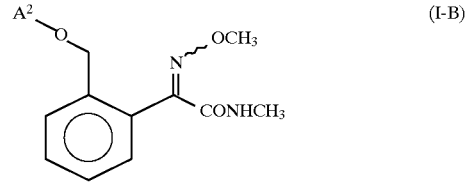

wherein $A^2$ is 3-chloro-2-pyridyl, 5-chloro-2-pyridyl, 3-trifluoromethyl-2-pyridyl, 4-trifluoromethyl-2-pyridyl, 6-trifluoromethyl-2-pyridyl, 6-methoxy-2-pyridyl, 6-isopropoxy- 2-pyridyl, 6-methylthio-2-pyridyl, 5-chloro-3-trifluoromethyl-2-pyridyl, 6-methoxy-3-trifluoromethyl-2-pyridyl, 6-isopropoxy-3-trifluoromethyl-2-pyridyl, 6-chloro-4-trifluoromethyl-2-pyridyl, 3,5,6-trichloro-4-trifluoromethyl-2-pyridyl, 6-chloro-3,5-di(trifluoromethyl)-2-pyridyl, 6-methoxy-5-trifluoromethyl-2-pyridyl, 6-isopropoxy-5-trifluoromethyl-2-pyridyl, 6-methylamino-5-trifluoromethyl-2-pyridyl, or 3,6-dichloro-5-trifluoromethyl-2-pyridyl, and ~ indicates a configuration of an E- or Z-isomer or a mixture thereof, or a salt thereof.

2. A compound according to claim 1, wherein $A^2$ is 3-trifluoromethyl-2-pyridyl or 5-chloro-3-trifluoromethyl-2-pyridyl, or a salt thereof.

3. A fungicidal composition which comprises as an active ingredient a compound of the formula (I-B) as claimed in claim 2 or a salt thereof.

4. A composition for controlling *Pseudocercosporella herpotrichoides*, which comprises as an active ingredient a compound of the formula (I-B) as claimed in claim 2 or a salt thereof.

5. A composition for controlling *Pseudocercosporella herpotrichoides*, which comprises as an active ingredient a compound of the formula (I):

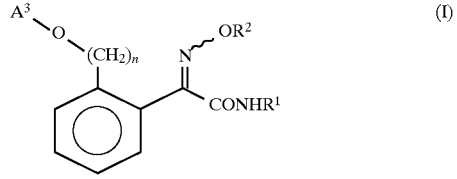

wherein $A^3$ is, optionally substituted pyridyl, $R^1$ and $R^2$ are the same or different and are alkyl, n is 1, and ~ indicates a configuration of an E- or Z-isomer or a mixture thereof, or a salt thereof.

6. A composition according to claim 5, wherein $R^1$ and $R^2$ are methyl.

7. A composition according to claim 4, wherein $A^2$ of the formula (I-B) is 3-chloro-2-pyridyl, 5-chloro-2-pyridyl, 3-trifluoromethyl-2-pyridyl, 4-trifluoromethyl-2-pyridyl, 6-trifluoromethyl-2-pyridyl, 6-methoxy-2-pyridyl, 6-isopropoxy-2-pyridyl, 6-methylthio-2-pyridyl, 5-chloro-3-trifluoromethyl-2-pyridyl, 6-methoxy-3-trifluoromethyl-2-pyridyl, 6-isopropoxy-3-trifluoromethyl-2-pyridyl, 6-chloro-4-trifluoromethyl-2-pyridyl,3,5,6-trichloro-4-trifluoromethyl-2-pyridyl, 6-chloro-3,5-di(trifluoromethyl)-2-pyridyl, 6-methoxy-5-trifluoromethyl-2-pyridyl, 6-isopropoxy-5-trifluoromethyl-2-pyridyl, 6-methylamino-5-trifluoromethyl-2-pyridyl or 3,6-dichloro-5-trifluoromethyl-2-pyridyl.

8. A composition according to claim 7, wherein $A^2$ is 3-trifluoromethyl-2-pyridyl or 5-chloro-3-trifluoromethyl-2-pyridyl.

* * * * *